(12) United States Patent
Bellantone

(10) Patent No.: US 8,679,052 B2
(45) Date of Patent: Mar. 25, 2014

(54) METHOD FOR ACCURATELY DETERMINING CONCENTRATIONS OF DIFFUSIBLE MATERIALS

(76) Inventor: Robert Arthur Bellantone, Yonkers, NY (US)

( * ) Notice: Subject to any disclaimer, the term of this patent is extended or adjusted under 35 U.S.C. 154(b) by 764 days.

(21) Appl. No.: 12/806,756

(22) Filed: Aug. 21, 2010

(65) Prior Publication Data

US 2011/0046890 A1    Feb. 24, 2011

Related U.S. Application Data

(60) Provisional application No. 61/274,994, filed on Aug. 24, 2009.

(51) Int. Cl.
 *A61M 1/16*    (2006.01)
(52) U.S. Cl.
 USPC .............................................. 604/28; 604/27
(58) Field of Classification Search
 USPC ............................... 600/366; 210/645; 702/19
 See application file for complete search history.

(56) References Cited

U.S. PATENT DOCUMENTS

| | | | |
|---|---|---|---|
| 6,346,090 B1* | 2/2002 | Liska et al. | 604/29 |
| 6,632,315 B2* | 10/2003 | Liska et al. | 156/244.13 |
| 6,904,309 B2* | 6/2005 | Derendorf et al. | 600/427 |
| 2001/0015253 A1* | 8/2001 | Liska et al. | 156/244.13 |
| 2002/0123676 A1* | 9/2002 | Haueter et al. | 600/309 |
| 2003/0020607 A1* | 1/2003 | Risi | 340/540 |
| 2005/0119588 A1* | 6/2005 | Model et al. | 600/581 |
| 2007/0292492 A1* | 12/2007 | Friden | 424/448 |
| 2009/0054854 A1* | 2/2009 | Hochmuth et al. | 604/265 |
| 2010/0021932 A1* | 1/2010 | Bellantone | 435/7.1 |
| 2010/0113975 A1* | 5/2010 | Kuennecke et al. | 600/573 |

OTHER PUBLICATIONS

Kabir, Mohammed Anowarul, Development of a pulsatile microdialysis method: Theory and application to the determination of U drug diffusion coefficients, Oct. 2003, Ph.D. dissertation, Long Island University, The Brooklyn Center, United States—New York from ProQuest Dissertations & Theses: Full Text database, Full document.*

Kabir, Mohammed Anowarul, Develpment of a pulsatile microdialysis method: Theory and application to the determination of U drug diffusion coeffcients, Oct. 2003, Ph.D. dissetation, Long Island University, The Brooklyn Center, United States—New York from Proquest Dissertation & Theses: Full Text database, Full document.*

* cited by examiner

*Primary Examiner* — Sujoy Kundu
*Assistant Examiner* — Corey Bailey
(74) *Attorney, Agent, or Firm* — Jean B. Mauro

(57) ABSTRACT

The invention provides an improved microdialysis method for determining the free concentration of an agent or drug (defined as the concentration of agent that is dissolved and free to diffuse, and not undissolved or precipitated, complexed, bound, included in micelles or microemulsions, etc.). In addition. the invention provides such a method under conditions in which the properties of the microdialysis probe may change.
Further, the invention provides a method for determining the permeability of a diffusible agent through the probe wall.
The invention also provides a method for determining the rate of change of concentration of an agent in a medium.

4 Claims, 1 Drawing Sheet

Schematic diagram of microdialysis probe.

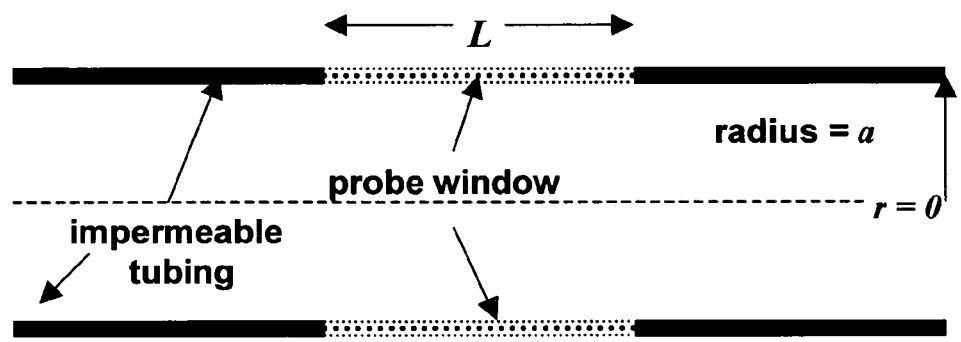
Schematic diagram of microdialysis probe.

US 8,679,052 B2

METHOD FOR ACCURATELY DETERMINING CONCENTRATIONS OF DIFFUSIBLE MATERIALS

CROSS-REFERENCE TO RELATED APPLICATION

This invention claims priority of U.S. provisional patent application No. 61/274,994, filed Aug. 24, 2009.

BACKGROUND OF THE INVENTION

1. Field of the Invention

The invention relates to an improved method of effecting and measuring mass transfer. In particular, the invention relates to the use of an improved method of microdialysis for measuring the transfer of relatively small quantities of dissolved, suspended or otherwise dispersed material between two media (one inside and one outside the microdialysis probe). The transfer can be characterized by the loss of material from the medium in which it is contained and/or the collection by the other medium, and in particular can be used to sample drug concentrations and/or characterize the rates at which various processes occur and the extent of transfer. Examples include determination of drug solubility, and processes such as binding of drugs to proteins, chelation and complexation of drugs, adsorption of drugs in solution onto charcoal and other adsorbing agents, and release of drugs from emulsions and microemulsion systems. In addition, the rate of transfer can be used to determine the diffusion coefficients of drugs and permeabilities of coatings placed on the probe window. (Although these examples involve drugs and are of pharmaceutical interest, the invention extends to any chemical, particle or droplet that can transfer between two media by passing through a membrane). Other applications include determining drug dissolution rates, and precipitation/crystallization rates of a dissolved drug from supersaturated solutions. Other applications within the scope and intent of the invention will occur to those skilled in the art.

2. Summary of the Prior Art

Microdialysis performed in a continuous manner is a known method for sampling drug concentrations from media in biological tissues or in vitro systems; however, certain deficiencies, as will be discussed more fully below, have prevented its optimum application. The prior art technique is based on the dialysis principle, employing a "semipermeable" membrane, i.e., one that is highly permeable to water and small molecules. In this method, a sampling solution (dialysate) is perfused continuously through a probe, and a drug or other material of interest passively diffuses into the dialysate from the surrounding medium. The dialysate is collected and analyzed for drug content, and the concentration of drug or other material of interest in the surrounding medium is then estimated from that information. (An analogous procedure can be done in which the dialysate is the donor, and the amount of drug lost to the surrounding medium is determined. This is often referred to as retrodialysis or retromicrodialysis.)

Microdialysis can offer significant advantages compared to other sampling methods. For instance, since microdialysis probes are very small, they can be placed directly into biological tissue for in vivo testing or into small "receivers" for in vitro systems. In addition, the method offers the advantage of a clean aqueous sample without pre-detection sample preparation, such as separation or clean up steps. Consequently, microdialysis is becoming a standard technique for in vivo and in vitro analysis of drug and biochemical concentrations.

In the standard microdialysis method, dialysate is continuously perfused through the probe, usually at a constant flow rate. (This will be referred to as continuous flow microdialysis, or CFMD.) For purposes of this invention, the membrane will be referred to as highly permeable, i.e., it is permeable to water and relatively small molecules, particles and droplets (e.g., from a microemulsion) but impermeable to relatively large molecules such as proteins, etc. The essential parameter, of course, is that the membrane be permeable with respect to the material, e.g., a drug, that is to be measured or withdrawn by means of diffusion. The choice of perfusion flow rate for the dialysate is governed primarily by the sample size for the analysis. Typical CFMD perfusion flow rates range from 0.5 to 2.0 µL/min for samples that will be analyzed by high-pressure liquid chromatography (HPLC) methods, for example. At these flow rates, however, the time required for sampling is relatively long, and the time resolution of the samples (i.e., the ability to associate a specific concentration with a specific time or a short time interval) is poor. In addition, there are problems associated with generating sufficient sample volumes (5-20 µL) in short time intervals (less than 30 seconds, perhaps less than 5-10 seconds). For instance, the sample concentrations become very dilute and may fall below the detection limit of the assay being utilized. Consequently, CFMD is poorly suited for studies in which concentrations change relatively rapidly. Such cases arise frequently in pharmacy and biology, and can include in vitro cellular drug uptake kinetics studies or binding studies, drug complexation, drug adsorption to charcoal or other binding agents, precipitation from supersaturated solutions, etc. For example, it has been reported that methazolamide uptake by red blood cells suspended in buffer is very rapid at early times, with the buffer concentration decreasing by 50% in the first 1-2 minutes. For other systems, such as protein binding, a 50% decrease in concentration may occur in less than 10-15 seconds. For setups like these, the inability of CFMD to sample every 10-15 seconds is a great disadvantage. In addition, for sampling methods such as spiking, which requires separating the cells from the buffer, large errors can potentially occur because the uptake process continues during the sample preparation. Thus, a microdialysis method that can offer good time resolution within relatively short time frames would offer significant advantages for systems like these.

Another problem that can be associated with CFMD is that, at typical perfusion flow rates, the recovery of drug and the resulting sampling efficiency can be poor. The recovery of a drug is the relationship between concentrations of the drug in the donor fluid and that of the dialysate, and the fraction recovered ($F_R$) is defined in terms of the ratio of the dialysate concentration ($C_S$) and free donor concentration ($C_{D,f}$). (The free donor concentration is defined as the concentration of dissolved and freely diffusible drug. Thus, it excludes the amounts of drug that are undissolved, bound, complexed, in micelles or microemulsions, etc.) For dialysate initially void of drug, and when $C_{D,f}$ can be taken as constant, this is given as $$F_R = \frac{C_S}{C_D} \qquad (1)$$

In vitro, a number of parameters influence the $F_R$, including the temperature, flow rate, probe length, and the physical properties of the drug, perfusate and membrane. Since the perfusion is continuous in CFMD, equilibrium between the dialysate and the donor medium is not approached, and the $F_R$ is typically low.

For retrodialysis, the analogous parameter would be the fraction remaining in the dialysate, $R_F$. Denoting the concentration in the dialysate before entering the probe as $C_0$, this is defined as $$R_F = \frac{C_S}{C_0} \quad (2)$$

For situations in which the concentration of the external medium changes appreciably during the time a microdialysis sample is taken, the $F_R$ defined above is not applicable because $C_D$ is changing with time. Thus, a method for determining the $C_D$ at specific times is needed. As discussed above, this is further complicated by the fact that taking samples rapidly is often difficult because processes can be ongoing during separation or other cleanup steps prior to sample assay. Thus, the need for a method to obtain specific values of $C_D$ at specific times using a fast method is apparent.

BRIEF DESCRIPTION OF THE DRAWINGS

FIG. 1 is a schematic diagram of a microdialysis probe useful in this invention.

SUMMARY OF THE INVENTION

The invention comprises a method for transferring (withdrawing or donating) by diffusion at least some of a diffusible material (hereinafter variously called an agent or drug) contained (either dissolved or suspended) in a medium either inside or outside of a microdialysis probe. As used herein, "diffusible" means able to diffuse in or through a fluid medium.

More specifically, the invention provides a method for determining the free concentration of an agent of drug (defined as the concentration of agent that is dissolved and free to diffuse, and not undissolved or precipitated, complexed, bound, included in micelles or microemulsions, etc.).

In its broadest sense, the invention relates to pumping a dialysate in a pulsed manner and analyzing at least some of such dialysate for its content of a desired material. More specifically, the invention relates to a microdialysis process comprising pumping a dialysate through a probe, with an improvement comprising pumping the dialysate in a pulsed manner and analyzing at least some of such dialysate for its content of a desired material.

In essence, the invention provides a method for accurately determining the diffusible or free concentration of an agent in a medium, comprising:
 a) providing a probe, for which the window volume $V_W$ and inner radius $\alpha$ and parameter $\lambda$ are known, comprising a section of relatively highly permeable membrane relative to any materials to which the membrane is attached for support and positioned between an inlet to a source of dialysate and an outlet to a receptacle and through which membrane the diffusible agent is to be transferred;
 b) putting said probe in contact with said medium;
 c) perfusing a known quantity of a dialysate into the relatively highly permeable section of the probe at a specified flow rate Q;
 d) allowing said known quantity of dialysate to remain stationary for a specified resting time $t_R$;
 e) flushing out said known quantity of dialysate with a single pulse to collect a sample of dialysate of a known volume $V_S$ into said receptacle at the same flow rate used in step (c), above;
 f) determining the concentration of said diffusible agent in said dialysate;
 g) calculating the apparent recovery $F_R^{App}$;
 h) repeating steps (c) through (g) with the same flow rate and sample volume but at least one different resting time;
 i) determining the value of $f_D$, $F_{RQ}$ and $\gamma_1$ for the probe using a chosen sample volume and flow rate from $F_R^{App}$ vs. exposure time;
 j) calculating the free concentration in the donor as $C_{D,f} = f_D C_D$.

By extension of the above detailed method as further provided in the claims hereof, it is also possible to determine the free concentration of an agent in a medium in which the properties of the microdialysis probe may change. It is further possible to determine the permeability of such an agent through the probe wall. In addition, it is possible to determine the rate of change of free concentration of the agent.

DISCUSSION OF THE INVENTION

The approach taken by the instant invention to solving the problems associated with the conventional microdialysis method, referred to as continuous flow microdialysis (CFMD), is the use of a novel method of microdialysis, referred to as pulsatile microdialysis (PMD). In this method, the dialysate is pumped into the probe and then allowed to remain at rest for a brief, discrete period referred to as the resting time ($t_R$). After a suitable $t_R$ (typically 3-100 seconds, preferably 3-15 seconds), the dialysate is flushed (i.e., pumped) out and collected for assay. It is usually preferred that this flushing is done as a single pulse at a relatively high flow rate (typically 50-165 µL/min), preferably to minimize or eliminate the effects of further diffusion, which usually simplifies mathematical analysis of the data. The PMD method allows flexibility to optimize the experimental procedure. For instance, the $t_R$ can be chosen to be long enough to give an acceptable amount of transfer between the dialysate and external medium by diffusion, and short enough to provide the desired time resolution. In addition, the volume that is flushed (i.e., the sample volume) is chosen to completely collect the sample that was at rest in the probe window while minimizing its dilution. For determining the concentration in the external medium, the resting time must be chosen to be long enough to allow enough of the drug to be collected by the dialysate, which is characterized by the fraction recovered $F_R$, which was defined by Equation (1). By analogy, when the dialysate is being used as the donor medium, the time must be long enough so some fraction of the drug in the dialysate is lost to the external medium, as given by Equation (2) for $R_F$). As a result, the PMD method offers two advantages over CFMD: First, the pulsatile method shows excellent time resolution, even for rapidly changing concentrations; second, the $F_R$ can be made higher with PMD by increasing the $t_R$, which can enable the detection of low concentrations of drug in the surrounding fluids using shorter time intervals than would be possible using CFMD.

The PMD process of drug exchange between the donor and dialysate is modeled as a diffusion process. Thus, the modeling tracks only the drug or other agent that is dissolved and freely diffusible, also referred to as 'free.' (Here, free is taken to mean the drug or agent is dissolved and able to diffuse through the probe window wall and exchange between the donor and dialysate. To be in the free form, it is assumed that the drug or other agent is not be precipitated or undissolved, complexed or otherwise bound to other molecules or particles, not incorporated into micelles, microemulsions, void spaces in particles, etc.)

When drug molecules are added to a solvent and there is no binding, complexation, trapping, precipitation, etc., the total drug concentration should be the same as the free drug concentration. However, for many systems this is not the case. Examples include multiphase systems, such as micelles, microemulsions, suspensions containing undissolved particles, cyclodextrin complexes, etc. Other examples include solutions in which drug molecules are bound to proteins, complexed with polymers, etc. For these cases, it is important to distinguish between the total concentration of drug or agent in the donor $C_D$ and the free concentration $C_{D,f}$. (For example, in drug delivery and therapeutics, only the free drug can distribute in the body and bring about a pharmacological effect.)

Experimentally, in the absence of degradation or loss, $C_D$ can be calculated as the total drug or agent added to the media in the donor vessel divided by the donor volume. In addition, the amount of drug present in a PMD sample can be determined by assay. From these, it is possible to determine the free concentration.

GLOSSARY OF TERMS $\alpha$ inner radius of the microdialysis probe window
A area of the probe window=$2\pi\alpha L$
$\beta_n$ roots of Equation (8)
CFMD continuous flow microdialysis
$C_D$ total concentration in the donor medium
$C_{D,f}$ dissolved free concentration in the donor medium
$C_0$ concentration in dialysate before entering probe
$C_S$ average concentration in a collected dialysate sample (=$M/V_S$)
D diffusion coefficient of the drug in the dialysate
$\delta_n$ defined by Equation (18)
$f_D$ defined by Equation (3)
$F_R$ fractional recovery for a sample, defined by Equation (1)
$F_R^{App}$ apparent fractional recovery, defined by Equation xxxxx
$F_{RQ}$ fractional recovery of the continuous portion of the PMD sample
$F_{RP}$ fractional recovery of the pulsed portion of the PMD sample
$\gamma_n$ defined by Equation (17)
h thickness of the wall of the probe window (outer minus inner radius)
L length of the microdialysis probe (=$V_W/\pi\alpha^2$)
$\lambda$ defined by Equation (9)
M total amount of drug in the collected a dialysate sample
$M_Q$ amount of drug in the sample portion that did not rest in the probe window
$M_P$ amount of drug in the sample portion that rested in the probe window
PMD pulsatile microdialysis
Q flow rate (μL/min)
$t_P$ exposure time for the pulsed portion of the dialysate sample ($t_R+t_Q$)
$t_Q$ transit time for the continuous portion of the dialysate sample=$V_W/Q$
$t_R$ resting time for dialysate in the probe window
$t_S$ duration of sampling time interval=$V_S/Q$
$\tau$ tortuosity of pores in the probe window wall
$V_W$ probe window volume=$\pi\alpha^2 L$ (same as the volume of dialysate allowed to rest)
$V_S$ volume of one dialysate sample Pulsatile Microdialysis: Mathematical Model for a Constant Concentration in the Medium Outside the Probe During a Sampling Interval PMD and microdialysis in general are based on the notion that drug in a diffusible form can exchange between a medium outside the probe and the dialysate inside the probe. Thus, the diffusion equations assume that the drug or other molecule is in a diffusible form, which physically requires that it be dissolved and free (i.e., not undissolved or precipitated, complexed, bound, adsorbed, in micelles or microemulsions, etc.). Any drug or other molecule that is in its dissolved and freely diffusible form will also be referred to as being free, and the concentration of drug or other molecule in that form will be referred to as the free concentration. When the molecule is in the donor medium outside the probe, the free concentration will be denoted by $C_{D,f}$ (free donor concentration. The total donor concentration, denoted by $C_D$, will refer to the total amount of drug or other molecule per volume in the donor, where the total includes the free, undissolved, bound, complexed, adsorbed, in micelles and microemulsions, etc.

In what follows, the free and total donor concentrations will be related using a fractional factor denoted as $f_D$, which is defined as $$f_D = \frac{C_{D,f}}{C_D} \quad (3)$$

In this section, the case is considered for which all of the or molecule to be sampled from the donor is dissolved and freely diffusible (also referred to as the free concentration). Here, dissolved and freely diffusible (or free) will be taken to mean that the drug or other molecule is dissolved in the donor medium and molecularly dispersed (or nearly so), so it is not precipitated (undissolved), bound to proteins or other complexing agents, incorporated in micelles or microemulsions, etc. Thus, the molecules are free to diffuse across the dialysis membrane that makes up the probe window wall (as defined below) and thus can move between the donor medium outside the probe and the dialysate medium inside the probe, as described below.

A prototype microdialysis setup is shown in FIG. 1, which illustrates a probe window made of a highly permeable tube of constant inner radius $\alpha$, length L and volume $V_W$. In the most general case, microdialysis can be described in cylindrical coordinates as a transport of drug that occurs by a combination of passive diffusion in the radial direction, and convection plus passive diffusion in the axial direction. This is written mathematically as $$\frac{\partial C}{\partial t} = -v_z\frac{\partial C}{\partial z} + D\frac{\partial^2 C}{\partial z^2} + \frac{D}{r}\frac{\partial}{\partial r}\left(r\frac{\partial C}{\partial r}\right)$$

Here, C is the concentration of the dialysate inside the probe at a given position and time, D is the diffusion coefficient of the drug in the dialysate, and $v_z$ is the axial velocity, which in general is a function of r but is typically (i.e., for CFMD) held constant with respect to time. On the right hand side, the first term represents the effects of convection, while the second and third terms represent the contribution the axial and radial diffusion, respectively. For the case of PMD, the following simplifications can be made:

While the dialysate is stationary in the probe, $v_z=0$ and the convection term can be ignored.

The dialysate is moved into and out of the probe window quickly and completely. Thus, the exposure time (the time spent inside the probe window, and where diffusion can occur into or out of the probe) for any portion of the dialysate sample is well defined.

The exposure time of the sample is chosen to be short enough to neglect axial diffusion. From the theory of separation of variables, for a tube of radius α, the relaxation time characteristic of the approach to equilibrium for diffusion in the radial direction is $\sim \alpha^2/D$ (Carslaw and Jaeger, *Conduction of Heat in Solids*, Clarendon Press, Oxford, 1985). From random walk theory, the average distance traveled by diffusing molecules during a time interval t is $\sim \sqrt{Dt}$ (Reichl, *A Modern Course in Statistical Physics*, U. Texas Press, Austin, 1980, Chapter 6). When the exposure time is comparable to the relaxation time, the average axial distance traveled due to diffusion is $\sim \alpha$. Since $\alpha \ll L$ for microdialysis probes, axial diffusion will have a negligible effect on the mass balance in the sample.

Even when the dialysate is being flushed, the exposure time for the flowing sample is short enough so the axial gradient does not have time to develop, and the $$v_z \frac{\partial C}{\partial z}$$

may be neglected.

As a result, the above equation reduces to $$\frac{\partial C}{\partial t} = \frac{D}{r} \frac{\partial}{\partial r}\left(r \frac{\partial C}{\partial r}\right) \quad (4)$$

Equation (4) is a partial differential equation that requires one initial condition and two boundary conditions for its complete solution. The initial condition is that the dialysate is initially void of drug (or other material to be separated) when it enters the probe region of the microdialysis tube. The boundary conditions are, in part, obtained from the following considerations:

The concentration in the medium outside the probe is constant (or may be approximated as constant) during each sampling period.

The drug concentration is finite everywhere in the microdialysis probe.

The dialysis tube wall is very thin and highly permeable, so pseudo-steady-state in the wall is established quickly. Thus, the flux of drug from the donor into the dialysate is proportional to the concentration difference across the wall of the probe window. The proportionality factor is the permeability P of the probe window, which is assumed to remain constant. The permeability is defined by the equation $$\frac{dM}{dt} = AP(C_{Donor} - C_{Receiver}) \quad (5)$$

where dM/dt is the rate at which the drug crosses the probe window wall, A is the area of the probe window, and $(C_{Donor} - C_{Receiver})$ is the difference in dissolved free concentrations across the membrane (i.e., the difference in dissolved free concentrations in the two liquid media at the inner and outer surfaces of the membrane).

Two cases will be considered below. The first is the case in which the donor is the medium outside the probe and the dialysate accumulates drug from the donor. The second is the case in which the dialysate is the donor and loses drug to the medium surrounding the probe.

The Donor Medium is Outside the Probe

When the medium outside the probe is the donor, then $C_{D,f}$ corresponds to the free concentration outside the probe and $C_R$ is the concentration in the dialysate near r=α. For this case, the boundary and initial conditions are mathematically written as Initial condition $\quad C(r, 0) = 0 \quad t = 0 \quad$ (6)

Boundary conditions $\quad C(0, t) = \text{finite} \quad r = 0$ $$-D \frac{\partial C}{\partial r} = P(C_{D,f} - C) \quad r = a$$

Using the separation of variables method, Equations (4) and (6) can be solved to give the concentration in a volume element of dialysate at a given radius as $$C(r, t) = C_{D,f}\left[1 - 2\sum_{n=1}^{\infty} \frac{\lambda J_0(\beta_n r/a)}{(\beta_n^2 + \lambda^2)J_0(\beta_n)} \exp\left(-\frac{\beta_n^2 Dt}{a^2}\right)\right] \quad (7)$$

Here, t is the length of time that a given volume element of dialysate was in the probe window (the exposure time), $J_0$ and $J_1$ are the zero-order and first-order Bessel function of the first kind, respectively (Carslaw and Jaeger, op. cit.; Ozisik, *Boundary Value Problems of Heat Conduction*, Dover Publications, New York, 1989), and the $\beta_n$ are the roots of the equation $$\beta_n J_1(\beta_n) - \lambda J_0(\beta_n) = 0 \quad (8)$$

$$\text{where } \lambda = \frac{aP}{D} \quad (9)$$

Values of $\beta_n$ have been tabulated for various values of λ and n in the literature (Crank, *The Mathematics of Diffusion*, Clarendon Press, Oxford, 1975), and can also be calculated from Equation (8) using the nonlinear solvers included with spreadsheets such as EXCEL®. For the probes used here, it can be assumed that the drug does not partition into the probe material, and thus permeates the probe window wall exclusively through pores. If the donor and receiver media are similar, the partition coefficients between the pore medium and the donor or dialysate may be taken as unity. Thus, denoting the probe window porosity, thickness (difference between the outer and inner radii) and tortuosity by ε, h and τ, respectively, the permeability of the window is given by $$P = \frac{\varepsilon D}{\tau h} \quad (10)$$

which can be combined with Equation (9) to give $$\lambda = \frac{a\varepsilon}{\tau h} \quad (11)$$

Thus, for these probes, λ depends on properties of the probe window, but not properties of the drug or solvent. However, this is a special case of Equation (9). If the probes are coated or modified, then λ depends not only on the geometrical properties of the probe, but also the material interactions between the drug and probe, and Equation (9) must be used.

The total amount of drug collected by the dialysate in the probe window after a given exposure time is found by integrating the concentration over the volume of the sample. Since the axial dependence is neglected in the mass balance, the mass in a sample of volume V with an exposure time t can be found from $$M' = \frac{V}{\pi a^2} \int_0^a 2\pi r C(r, t) dr \quad (12)$$

Not all parts of a collected dialysate sample will be exposed to the donor for the same length of time, and two portions must be considered. One portion of the sample (referred to as the continuous portion) flows through the probe window without resting. The other portion (referred to as the pulsed portion) is pumped into the window, allowed to remain at rest for a resting time $t_R$, and then pumped out. For the continuous portion, the dialysate exposure time is simply the transit time $t_Q$ required for an element of fluid to move through the probe window. The exposure time $t_P$ for the pulsed portion is the sum of the resting and transit times. These are given, respectively, by $$t_Q = \frac{V_W}{Q} \text{ and } t_P = t_R + t_Q \quad (13)$$

where Q is the flow rate (volume per time) of the flushing. Thus, for a sample of volume $V_S$, the pulsed portion has a volume $V_W$ and accumulates a mass $M_P$ during a total exposure time of $t_P$, while the continuous portion has a volume $V_S - V_W$ and accumulates a mass $M_Q$ during an exposure time of $t_Q$. $M_P$ can be found by setting $t=t_P$ in Equation (7), performing the integration in Equation (12), and multiplying by the length of the probe window $V_W/\pi a^2$. $M_Q$ can be found by setting $t=t_Q$ in Equation (7), performing the integration in Equation (12), and multiplying by a length $(V_S-V_W)/\pi a^2$. The total mass of drug M in a collected sample is given by $$M_S = M_P + M_Q \quad (14)$$

where $$M_P = V_W C_{D,f} \left[1 - \sum_{n=1}^{\infty} \delta_n \exp(-\gamma_n t_P)\right] \quad (15)$$

$$M_Q = (V_S - V_W) C_{D,f} \left[1 - \sum_{n=1}^{\infty} \delta_n \exp(-\gamma_n t_Q)\right] \quad (16)$$

The constants $\gamma_n$ are $\delta_n$ are given by $$\gamma_n = \frac{\beta_n^2 D}{a^2} \quad (17)$$

$$\delta_n = \frac{4\lambda^2}{\beta_n^2(\beta_n^2 + \lambda^2)} \quad (18)$$

where $$\sum_{n=1}^{\infty} \delta_n = 1 \quad (19)$$

(It should be noted that this form of $\gamma_n$ holds only for dialysate solutions. For two-phase systems, such as microemulsions, the form of $\gamma_n$ may change, but the use of γ in the subsequent equations is expected to remain the same.)

When the concentration in the external medium is constant while taking a sample, or can be approximated as constant, the fractional recovery in the sample, defined in Equation (1), can be expressed in terms of the mass in the sample and the sample volume as $$F_R = \frac{M_S}{V_S C_{D,f}} \quad (20)$$

$$M_S = V_S C_S$$

Similarly, the fractional recoveries of the pulsed ($F_{RP}$) and continuous ($F_{RQ}$) portions of the sample are defined as $$F_{RP} = \frac{M_P}{V_W C_{D,f}} = \left[1 - \sum_{n=1}^{\infty} \delta_n \exp(-\gamma_n t_P)\right] \quad (21)$$

$$F_{RQ} = \frac{M_Q}{(V_S - V_W) C_{D,f}} = \left[1 - \sum_{n=1}^{\infty} \delta_n \exp(-\gamma_n t_Q)\right] \quad (22)$$

The total mass in the sample can be written as $$M_S = V_W C_{D,f} F_{RP} + (V_S - V_W) C_{D,f} F_{RQ} \quad (23)$$

Thus, $M_S$ is proportional to the free donor concentration $C_{D,f}$ and linear calibration plots relating $C_D$ and $C_S$ can be constructed according to Equation (1). It is also possible to rewrite Equation (23) as $$F_R = \frac{V_W}{V_S}(F_{RP} - F_{RQ}) + F_{RQ} \quad (24)$$

For a constant flow rate, $F_{RQ}$ corresponds to the fractional recovery for CFMD, as can be seen from Equations (21), (22) and (24) when $t_P=t_Q$, (equivalently, $t_R=0$). This provides a procedure for obtaining the $F_{RQ}$ from $F_R$ data according to the condition that $$F_{RQ} = \lim_{t_R \to 0} F_R \tag{25}$$

This can be done in practice by fitting the $F_R$ vs. $t_R$ to an empirical function using nonlinear regression, and then taking the value of the function for $t_R=0$. Since the above theory predicts that $F_R$ varies exponentially with the exposure time, this is using the equations below:

$$F_R = \alpha_1 \exp(-b_1 t_R) + \alpha_2 \exp(-b_2 t_R) + \alpha_3 \tag{26}$$

$$F_{RQ} = \alpha_1 + \alpha_2 + \alpha_3 \tag{27}$$

Since $F_R$ and $F_{RQ}$ can be determined experimentally (see Equation (1) and Example 1, respectively), it is possible to obtain $F_{RP}$ for any exposure time $t_P$ from Equation (24). However, this requires accurately knowing the window volume $V_W$. In practice, when a probe is first used, it is calibrated to determine $V_W$, which then allows the $F_{RP}$ to be calculated in any subsequent experiment using that probe. (It should be noted that simply calculated $V_W$ using manufacturer's specifications or optical measurements is not accurate enough for many of the analyses presented here. Thus, it is preferred to measure $V_W$ by plotting $F_R$ vs. $1/V_S$, using a constant resting time with a known value of $F_{RP}$. This discussed more fully below.)

The approach to equilibrium is characterized in the above equations by the exponential transient terms in the infinite series. For all values of $\lambda$ and n, both the $\delta_n$ and exponential terms are between zero and one, and both tend toward zero with increasing n or time of exposure. Using typical values for the dialysis probes used in this study ($\alpha \sim 100\text{-}150\mu$, $h=8\text{-}12\mu$, $\epsilon<0.05$) and a typical tortuosity value ($\tau>1.5\text{-}2$), Equation (11) shows that $0<\lambda<0.5$. For this range of $\lambda$, numerical calculations show that $\delta_1>0.99$ and $\delta_2/\delta_1<0.005$. Thus, there is negligible error (less than 0.1-0.5%) introduced by neglecting the n>1 terms, so Equations (21) and (22) can be written as $$F_{RP} = \frac{M_P}{V_W C_D} = 1 - \delta_1 \exp(-\gamma_1 t_P) \tag{28}$$

$$F_{RQ} = \frac{M_Q}{(V_S - V_W)C_D} = 1 - \delta_1 \exp(-\gamma_1 t_Q) \tag{29}$$

$$\ln(1 - F_{RP}) = \ln \delta_1 - \gamma_1 t_P \tag{30}$$

where $$\gamma_1 = \frac{\beta_1^2 D}{a^2} = \frac{\pi L \beta_1^2 D}{V_W} \tag{31}$$

$$\delta_1 = \frac{4\lambda^2}{\beta_1^2(\beta_1^2 + \lambda^2)} \tag{32}$$

where $$\beta_1 J_1(\beta_1) - \lambda J_0(\beta_1) = 0 \tag{33}$$

and $F_{RP}$ is determined from Equation (24).

In theory, plots of $\ln(1-F_{RP})$ vs. $t_P$ can be used to determine $\gamma_1$ and $\delta_1$ (which, in turn, can be used in Equations (8) and (18) to find 2). This is true for finding $\gamma_1$ because small experimental errors will minimally affect the slope. However, the intercept is typically close to zero because $\delta_1$ is close to 1, so experimental errors can result in significant relative errors in the intercept. Because small errors in the value of $\delta_1$ can result in relatively large errors in the corresponding $\lambda$, the approximations are made that $$\delta_1 = 1 \text{ neglect n>1 terms} \tag{34}$$

$$F_{RP} = 1 - \exp(-\gamma_1 t_P) \tag{35}$$

$$F_{RP} = 1 - \exp(-\gamma_1 t_Q) \tag{36}$$

Since $\delta_1$ is taken as 1, only $\gamma_1$ is obtained from a plot of Equation (35). However, to accurately find the $F_{RP}$ and avoid possibly substantial errors in value of $\gamma_1$, it is necessary that the window volume $V_W$ be accurately known. (Methods to determine $V_W$ are presented below.) It is also possible to obtain $\gamma_1$ using an alternative method, which is given by Equation (47) below.

The probe window wall permeability coefficient can be calculated using PMD as well. From Equations (13), (28) and (34), the mass in the pulsed portion of the sample is given by $$M_P = V_W C_D F_{RP} = V_W C_D [1 - \exp(-\gamma_1 t_Q) \exp(-\gamma_1 t_R)]$$

Using Equation (14) and noting that $M_Q$ is constant when all samples are taken in the same manner, the rate of uptake of the drug into the dialysate is given by $$\frac{dM}{dt} = \frac{dM}{dt_R} = V_W C_D \gamma_1 \exp(-\gamma_1 t_Q) \exp(-\gamma_1 t_R)$$

Using Equation (29) gives $$\frac{dM}{dt} = V_W C_D \gamma_1 (1 - F_{RQ}) \exp(-\gamma_1 t_R)$$

If $t_R=0$, this can be written as $$\frac{dM}{dt} = V_W C_D \gamma_1 (1 - F_{RQ}) \tag{37}$$

At very early times ($t_R$ approaching zero), the receiver concentration $C_R$ (here, corresponding to the dialysate concentration near the probe membrane) is negligible compared to the donor concentration $C_D$ (corresponding here to the concentration in the external solution), and Equation (5) can be simplified to $$\frac{dM}{dt} = APC_D \tag{38}$$

Here, A is the area of the probe window, which can be obtained from $V_W$ and the length of the window L (which is easily measured). Combining Equations (37) and (38) leads to $$P = \frac{V_W \gamma_1 (1 - F_{RQ})}{A}$$

A refinement can be done as follows. The value of dM/dt in the limit of $t_P=0$ can be obtained graphically from a plot of M vs. $t_R$ by doing a best fit of the curve and extrapolating to $t_R=-t_Q$. This would correspond to $F_{RQ}=0$ and $C_R=0$. Thus, Equation (38) would hold exactly and the Equation (37) would be written as $$\frac{dM}{dt} = V_W C_D \gamma_1 \quad (39)$$

As a result, the permeability would be given as $$P = \frac{V_W \gamma_1}{A} \quad (40)$$

From the above, it is possible to obtain the diffusion coefficient D of a drug in the dialysate medium. Equations (8), (9) and (17) lead to $$\lambda = \frac{\beta_1 J_1(\beta_1)}{J_0(\beta_1)} \quad (41)$$

$$\gamma_1 = \frac{\beta_1^2 D}{a^2} \quad (42)$$

$$\frac{P}{\gamma_1 a} = \frac{J_1(\beta_1)}{\beta_1 J_0(\beta_1)} \quad (43)$$

Knowing P, α and $\gamma_1$ allows $\beta_1$ to be calculated from Equation (43), which then allows D to be calculated from Equation (42) and λ from Equation (9) or Equation (41).

As mentioned above, the volume of the probe window must be accurately known to obtain accurate values of the $F_{RP}$. Since optical measurements and using manufacturers' nominal specifications are not accurate enough, the methods presented here were developed to more accurately determine $V_W$.

If a long resting time is used in a PMD experiment, then the concentrations of the dialysate resting in the probe window and in the medium outside the probe will equilibrate, so $$F_R \to 1 \text{ long } t_R \quad (44)$$

and Equation (24) becomes $$F_R = F_{RQ} + V_W(1 - F_{RQ})\frac{1}{V_S} \quad (45)$$

A plot of $F_R$ vs. $1/V_S$ will give an intercept of $F_{RQ}$ and a slope of $V_W(1-F_{RQ})$, which will allow the calculation of $V_W$. ($F_{RQ}$ can also be measured independently from CFMD data.) A variation of this method that will not require long resting times is to obtain a matrix of $F_R$ vs. $1/V_S$ for a range of resting times, and perform a nonlinear regression on the matrix. However, the preferred method of using Equation (45) is preferred because it avoids the potential numerical problems associated with nonlinear regressions.

Another variation that would also avoid the need for long resting times is as follows. If all samples are taken in the same way, $V_S$ and $F_{RQ}$ are constant, and $V_W$ does not change. Thus, rewriting Equation (24) as $$F_R = \frac{V_W}{V_S} F_{RP} + \text{constant}$$

and taking the derivative gives $$\frac{dF_R}{dt_R} = \frac{V_W}{V_S} \frac{dF_{RP}}{dt_R} \quad (46)$$

Combining this with Equation (28) and approximating $\delta_1=1$, which is valid for microdialysis probes, gives $$\frac{dF_R}{dt_R} = \frac{V_W \gamma_1}{V_S} \exp(-\gamma_1 t_Q)\exp(-\gamma_1 t_R)$$

This derivative is always positive, and taking the natural log gives $$\ln\left(\frac{dF_R}{dt_R}\right) = -\gamma_1 t_R + k' \quad (47)$$

$$k' = -\gamma_1 t_Q + \ln\left(\frac{V_W \gamma_1}{V_S}\right) \quad (48)$$

where k' is a constant. From a plot of the natural log of the derivative vs. the resting time in Equation (47), $\gamma_1$ is obtained from the slope and $V_W$ can be obtained from the intercept. It should be noted, however, that this method gives good results for $\gamma_1$ but is not as good for obtaining $V_W$. In practice, $V_W$ is best obtained from Equation (24) by plotting $F_R$ vs. $1/V_S$ (described in Example 1, below). This can be then be used when obtaining $\gamma_1$ by taking the slope of Equation (47), subject to the constraint that the intercept k' be consistent with the value of $V_W$ obtained from the plot of Equation (24). This is easily done in Microsoft Excel® (using the Solver function) and other programs.

It should be noted that Equation (47) provides an alternative method for determining the parameter $\gamma_1$ from the slope of the log $(dF_R/dt_R)$ vs. $t_R$ or $t_P$ (since $t_P=t_R+t_Q$ leads to $dt_P=dt_R$ when $t_Q$ is constant). In practice, this method works well. It is typically done by fitting the $F_R$ vs. $t_R$ data to an empirical function (usually bi-exponential plus a constant), taking the derivative analytically, and then plotting the log of the derivative vs. $t_R$.

When the drug or other molecule is not entirely free, $C_{Df} < C_D$ and $f_D < 1$. This presents a problem because $C_S$ is known by assay and $C_D$ is known from the experimental setup (the total drug added per volume of donor), but the free drug concentration (thus, $f_D$) is not known. Thus, for multiphase systems, it is only possible to specify the apparent fractional recovery, denoted as $F_R^{App}$, which is defined as $$F_R^{App} = \frac{C_S}{C_D} \quad (49)$$

$F_R^{App}$ is the experimentally determined quantity, but it does not directly represent the mechanistic diffusion behavior of the system, because it is based on the total donor concentration, while only the free drug in the donor diffuses into the probe. The quantity that relates to the diffusion mechanism is the ratio of $C_S$ and the free donor concentration. This is referred to as the true fractional recovery, which is again denoted by $F_R$, and defined as $$F_R = \frac{C_S}{C_{D,f}} = \frac{M_S}{V_S C_{D,f}} \quad (50)$$

From Equations (3) and (49), the apparent and true fractional recoveries are related as $$F_R^{APP} = f_D F_R \quad (51)$$

Since $0 < f_D \le 1$, $F_R^{App} \le F_R$. When all of the drug is free, the free and total donor concentrations are the same, so $f_D = 1$ and the apparent and true fractional recoveries are the same ($F_R^{App} = F_R$).

The above generalizations lead to $$F_R^{App} = f_D \left[ \frac{(V_S - V_W)}{V_S} F_{RQ} + \frac{V_W}{V_S} F_{RP} \right] \quad (52)$$

$$F_R^{App} = f_D \left\{ \frac{V_W}{V_S} \left[ 1 - \sum_{n=1}^{\infty} \delta_n \exp(-\gamma_n t_P) \right] + \frac{(V_S - V_W)}{V_S} F_{RQ} \right\} \quad (53)$$

This equation is used for data fitting. To do that, $F_R^{App}$ is determined vs. the exposure or resting time, and profiles of $F_R^{App} = f_D F_R$ (profiles of in a manner similar to that discussed with regard to Equation, except the fits are done here using three parameters ($\gamma_1$, $F_{RQ}$ and $f_D$).

It is important to note that $f_D$ represents the ratio of free and total drug concentration in the donor. The mass fraction that is free can be calculated from $f_D$.

Numerical Procedure

The implementation of the above equations is described below and illustrated in the Examples. From Equation (53), it is possible to do fits using only $f_D$ and $\gamma_1$, then calculating all other parameters ($\gamma_n$, $\beta_n$, $F_{RQ}$) from the calibrated values of $\lambda$ and $V_W$. (Methods for such a calibration are discussed in copending U.S. patent application Ser. No. 12/460,606, filed Jul. 21, 2009, the disclosure of which is incorporated herein by reference.) However, better results are obtained using a three parameter fit and iterating on $f_D$, $\gamma_1$, and $F_{RQ}$, and that is the method used in practice. In addition, two cases arise: 1) The properties of the probe (e.g., permeability of the probe window wall) do not change. This occurs when the free concentration is well below the solubility of drug or other agent. 2) The properties of the probe (e.g., permeability of the probe window wall) change. This can happen when the concentration of drug or other agent is near or above its solubility, leading to precipitation of drug or agent in the pores of the membrane. This reduces the permeability and changes the value of $\lambda$.

In the first case, the calibrated values of $\lambda$ and $V_W$ are used and nonlinear regressions of $F_R^{App}$ vs. $t_P$ are done by iterating on $f_D$, $\gamma_1$, and $F_{RQ}$. In the second case, the calibrated values of $V_W$ is used, but $\lambda$ is assumed to have changed. As a result, nonlinear regressions of $F_R^{App}$ vs. $t_P$ are done by iterating on $\lambda$, $f_D$, $\gamma_1$, and $F_{RQ}$, subject to the constraint that the diffusion coefficient of the drug or agent D, for example as calculated from Equations (53), (8) or (31) or equivalent, equals a previously determined value. (In other words, the D is constant in the dialysate at a given temperature and does not depend on $\lambda$.)

EXAMPLE 1

Determination of Free Ibuprofen Concentration for a Donor Containing Ibuprofen and Tween 40 in Concentrations Above the CMC (Critical Micelle Concentration)

It is possible to measure the $F_{RQ}$ directly using CFMD data. Alternatively, it is possible to obtain this parameter using PMD data. In this application, the donor is outside the probe, and its concentration is taken as constant (so the $F_{RQ}$ is well defined).

An example of a method that uses PMD to determine $F_{RQ}$ is as follows:

a) Immerse a previously calibrated probe (for $\lambda$ and $V_W$, as given in patent application Ser. No. 11/591,083, filed Oct. 31, 2006, the disclosure of which is incorporated herein by reference) in a liquid donor medium outside the probe containing a known total concentration of ibuprofen (the diffusing agent) and Tween 40 (a nonionic surfactant). The volume of the external solution should be large enough (at least ~25 mL) so drug transfer to the dialysate will not change the external medium concentration.

b) Pump fresh dialysate (i.e., containing no drug) into the probe window. The dialysate should be the same liquid as the external medium. It is preferable that the flow rate Q be relatively high (at least ~100 μL/min), so that $F_{RQ}$ is much smaller than 1.

c) Allow the dialysate to occupy the probe at rest for a known time $t_R$.

d) Flush and collect a known sample volume $V_S$ of the dialysate at the same flow rate Q. $V_S$ must be sufficient to collect all of the dialysate that was at rest in the window.

e) Perform an appropriate assay (HPLC, etc.) to determine the concentration and amount of drug in the dialysate sample, and calculate the $F_R^{App}$ from Equation (49).

f) Repeat steps b) through e) using the same sample volume and flow rate, but for at least one (preferably at least four) different resting times.

g) Fit a plot of the $F_R^{App}$ vs. $t_P$ to the function given by Equation (53), iterating on $f_D$, $\gamma_1$, and $F_{RQ}$.

h) Calculate the free ibuprofen concentration using Equation (3).

EXAMPLE 2

Determination of Dissolved (Free) Concentration of Ibuprofen During Dissolution of Nanoparticles of Ibuprofen to Approach or Exceed the Drug Solubility in the Donor Medium The parameter $\lambda$ characterizes the transfer across the probe window and how that transfer affects the concentration of the agent in the dialysate. Preferably, $\lambda$ is 0-10, more preferably 0-3, still more preferably <0.3.

An example method to determine the parameter $f_D$ in a situation where $\lambda$ may change during the PMD experiment is as follows:

a) Make an aqueous buffer solution at low pH (for instance, pH=2, which is well below the $pK_a$ of ibuprofen of ~4.5). Immerse a PMD probe for which the window volume $V_W$ is already known by calibration.

b) While continuously stirring, add an amount of undissolved ibuprofen nanoparticles in a quantity sufficient to approach or exceed the solubility of the drug in the buffer solution. (This may result in drug precipitation in the pores of the microdialysis probe, and thus change λ and P.) This will be the donor solution.

i) Pump fresh dialysate (i.e., containing no drug) into the probe window. The dialysate should be the same liquid as the external medium. It is preferable that the flow rate Q be relatively high (at least ~100 μL/min), so that $F_{RQ}$ is much smaller than 1.

j) Allow the dialysate to occupy the probe at rest for a known time $t_R$.

k) Flush and collect a known sample volume $V_S$ of the dialysate at the same flow rate Q. $V_S$ must be sufficient to collect all of the dialysate that was at rest in the window.

l) Perform an appropriate assay (HPLC, etc.) to determine the concentration and amount of drug in the dialysate sample, and calculate the $F_R^{App}$ from Equation (49).

m) Repeat steps b) through e) using the same sample volume and flow rate, but for this example at least three (preferably at least four) different resting times.

n) Fit a plot of the $F_R^{App}$ vs. $t_P$ to the function given by Equation (53), and using Equation (8) and (31), for example, to iterate on λ, $f_D$, $γ_1$, and $F_{RQ}$, subject to the constraint that the value of D calculated from Equation (9) or (31) equals a previously determined value. (for instance, as described in patent application Ser. No. 11/591,083, filed Oct. 31, 2006.)

o) Calculate the dissolved (free) concentration using Equation (3)

I claim:

1. A method for accurately determining the diffusible or free concentration of an agent in a medium in which the properties of the probe may change, comprising:
   a) providing a probe, for which the window volume $V_w$ and inner radius α are known but the value of λ may change, comprising a section of relatively highly permeable membrane relative to any materials to which the membrane is attached for support and positioned between an inlet to a source of dialysate and an outlet to a receptacle, and through which membrane the diffusible agent is to be transferred;
   b) putting said probe in contact with said medium;
   c) perfusing a known quantity of a dialysate, for which the diffusion coefficient D of the diffusible agent is known, into the relatively highly permeable section of the probe at a specified flow rate Q;
   d) allowing said known quantity of dialysate to remain stationary for a specified resting time $t_R$;
   e) flushing out said known quantity of dialysate with a single pulse to collect a sample of dialysate of a known volume $V_S$ into said receptacle at the same flow rate used in step (c), above;
   f) determining the concentration of said diffusible agent in said dialysate;
   g) calculating the apparent recovery $F_R^{App}$;
   h) repeating steps (c) through (g) with the same flow rate and sample volume but at least one different resting time;
   i) determining the value of λ, $f_D$, $F_{RQ}$ and $γ_1$ for the probe using a chosen sample volume and flow rate from $F_R^{App}$ vs. exposure time, subject to the constraint that the diffusion coefficient of the diffusible agent in the dialysate equals its known value;
   j) calculating the free concentration in the donor as $C_{D,f}=f_D C_D$.

2. A method for accurately determining the permeability of a diffusible agent through the probe wall in a medium in which the properties of the probe may change, comprising:
   a) providing a probe comprising a section of relatively highly permeable membrane relative to any materials for which the window volume $V_W$ and inner radius α are known but the value of may change, to which the membrane is attached for support and positioned between an inlet to a source of dialysate and an outlet to a receptacle, and through which membrane the diffusible agent is to be transferred;
   b) putting said probe in contact with said medium;
   c) perfusing a known quantity of a dialysate, for which the diffusion coefficient D of the diffusible agent is known, into the relatively highly permeable section of the probe at a specified flow rate Q;
   d) allowing said known quantity of dialysate to remain stationary for a specified resting time $t_R$;
   e) flushing out said known quantity of dialysate with a single pulse to collect a sample of dialysate of a known volume $V_S$ into said receptacle at the same flow rate used in step (c), above;
   f) determining the concentration of said diffusible agent in said dialysate;
   g) calculating the apparent recovery $F_R^{App}$;
   h) repeating steps (c) through (g) with the same flow rate and sample volume but at least one different resting time;
   i) determining the value of λ, $f_D$, $F_{RQ}$ and $γ_1$ for the probe using a chosen sample volume and flow rate from $F_R^{App}$ vs. exposure time, subject to the constraint that the diffusion coefficient of the diffusible agent in the dialysate equals its known value;
   j) calculating the permeability coefficient of the agent through the probe wall as free concentration in the donor as P=λD/α.

3. A method for accurately determining the rate of change of diffusible or free concentration of an agent in a medium, comprising:
   a) providing a probe, for which the window volume $V_W$ and inner radius α and parameter λ are known, comprising a section of relatively highly permeable membrane relative to any materials to which the membrane is attached for support and positioned between an inlet to a source of dialysate and an outlet to a receptacle, and through which membrane the diffusible agent is to be transferred;
   b) putting said probe in contact with said medium;
   c) perfusing a known quantity of a dialysate into the relatively highly permeable section of the probe at a specified flow rate Q;
   d) allowing said known quantity of dialysate to remain stationary for a specified resting time $t_R$;
   e) flushing out said known quantity of dialysate with a single pulse to collect a sample of dialysate of a known volume $V_S$ into said receptacle at the same flow rate used in step (c), above;
   f) determining the concentration of said diffusible agent in said dialysate;
   g) calculating the apparent recovery $F_R^{App}$;
   h) repeating steps (c) through (g) with the same flow rate and sample volume but at least one different resting time;
   i) determining the value of $f_D$, $F_{RQ}$ and $γ_1$ for the probe using a chosen sample volume and flow rate from $F_R^{App}$ vs. exposure time;
   j) calculating the free concentration in the donor as $C_{D,f}=f_D C_D$;
   k) Repeating steps (c) through (j) at various times, and plotting $C_{D,f}$ vs. time.

4. A method for accurately determining the rate of change of diffusible or free concentration of an agent in a medium in which the properties of the probe may change, comprising:

a) providing a probe, for which the window volume $V_W$ and inner radius $\alpha$ are known but the value of $\lambda$ may change, comprising a section of relatively highly permeable membrane relative to any material to which the membrane is attached for support and positioned between an inlet to a source of dialysate and an outlet to a receptacle, and through which membrane the diffusible agent is to be transferred;

b) putting said probe in contact with said medium;

c) perfusing a known quantity of a dialysate, for which the diffusion coefficient D of the diffusible agent is known, into the relatively highly permeable section of the probe at a specified flow rate Q;

d) allowing said known quantity of dialysate to remain stationary for a specified resting time $t_R$;

e) flushing out said known quantity of dialysate with a single pulse to collect a sample of dialysate of a known volume $V_S$ into said receptacle at the same flow rate used in step (c), above;

f) determining the concentration of said diffusible agent in said dialysate;

g) calculating the apparent recovery $F_R^{App}$;

h) repeating steps (c) through (g) with the same flow rate and sample volume but at least one different resting time;

i) determining the value of $\lambda$, $f_D$, $F_{RQ}$ and $\gamma_1$ for the probe using a chosen sample volume and flow rate from $F_R^{App}$ vs. exposure time, subject to the constraint that the diffusion coefficient of the diffusible agent in the dialysate equals its known value;

j) calculating the free concentration in the donor as $C_{D,f} = f_D C_D$; Repeating steps (c) through (j) at various times, and plotting $C_{D,f}$ vs. time.

* * * * *